United States Patent
Hebblewhite et al.

[11] Patent Number: 6,135,432
[45] Date of Patent: *Oct. 24, 2000

[54] HUMIDIFIER

[75] Inventors: Malcolm Hebblewhite, Cremorne; Philip Rodney Kwok, West Pymble; Robert Edward Styles, Glenhaven; John William Ernest Brydon, Waverton, all of Australia

[73] Assignee: ResMed Limited, North Ryde, Australia

[ * ] Notice: This patent issued on a continued prosecution application filed under 37 CFR 1.53(d), and is subject to the twenty year patent term provisions of 35 U.S.C. 154(a)(2).

[21] Appl. No.: 08/918,004
[22] Filed: Aug. 25, 1997

Related U.S. Application Data

[63] Continuation of application No. 08/633,413, Jun. 10, 1996, abandoned.

[30] Foreign Application Priority Data

Jun. 8, 1995 [AU] Australia .................. 3440

[51] Int. Cl.⁷ .................................................. B01F 3/04
[52] U.S. Cl. ........................................ 261/119.1
[58] Field of Search ............................... 261/119.1

[56] References Cited

U.S. PATENT DOCUMENTS

| | | |
|---|---|---|
| 1,730,212 | 10/1929 | Iveland .................. 261/119.1 |
| 1,817,265 | 8/1931 | Pando .................... 261/119.1 |
| 1,869,344 | 7/1932 | Schonbein ............... 261/119.1 |
| 2,710,178 | 6/1955 | Froelich ................. 261/119.1 |
| 2,712,927 | 7/1955 | Blum . |
| 2,953,355 | 9/1960 | Hungate . |
| 3,659,604 | 5/1972 | Melville et al. . |
| 3,869,529 | 3/1975 | Follette . |
| 3,903,883 | 9/1975 | Pecina et al. . |
| 3,987,133 | 10/1976 | Andra . |
| 4,051,205 | 9/1977 | Grant . |
| 4,060,576 | 11/1977 | Grant . |
| 4,110,419 | 8/1978 | Miller . |
| 4,201,204 | 5/1980 | Rinne et al. . |
| 4,203,027 | 5/1980 | O'Hare et al. . |
| 4,346,048 | 8/1982 | Gates . |
| 4,389,353 | 6/1983 | Gates . |
| 4,448,035 | 5/1984 | Moriyama et al. . |
| 4,590,772 | 5/1986 | Nose et al. . |
| 4,595,139 | 6/1986 | Levine . |
| 4,621,632 | 11/1986 | Bartels et al. . |
| 5,163,423 | 11/1992 | Suzuki . |
| 5,231,979 | 8/1993 | Rose et al. . |
| 5,240,177 | 8/1993 | Muramatsu et al. . |
| 5,367,604 | 11/1994 | Murray . |
| 5,537,997 | 7/1996 | Mechlenburg et al. . |
| 5,558,084 | 9/1996 | Daniell et al. . |
| 5,564,415 | 10/1996 | Dobson eet al. . |
| 5,590,644 | 1/1997 | Rosenkoetter . |
| 5,590,648 | 1/1997 | Mitchell . |
| 5,598,837 | 2/1997 | Sirianne, Jr. et al. . |
| 5,673,687 | 10/1997 | Dobson et al. . |

FOREIGN PATENT DOCUMENTS

| | | |
|---|---|---|
| 9226120 | 7/1995 | Australia . |
| 298 367 A2 | 1/1989 | European Pat. Off. . |
| 481 459 A1 | 4/1992 | European Pat. Off. . |
| 0 535 952 A1 | 7/1993 | European Pat. Off. . |
| 0 845 277 | 6/1998 | European Pat. Off. . |
| 2 630 917 | 11/1989 | France . |
| 175793 | 10/1906 | Germany ................ 261/119.1 |
| 2439 | 9/1865 | United Kingdom ....... 261/119.1 |
| 1589 | 5/1874 | United Kingdom ....... 261/119.1 |
| 25866 | 1/1898 | United Kingdom ....... 261/119.1 |
| 1 294 808 | 11/1972 | United Kingdom . |
| WO 82/03326 | 10/1982 | WIPO . |
| WO 96/35911 | 11/1996 | WIPO . |
| WO 98/04311 | 2/1998 | WIPO . |

OTHER PUBLICATIONS

Respironics, Inc.; Oasis Humidity Operating Instruction; Jul. 17, 1996;.

*Primary Examiner*—C. Scott Bushey
*Attorney, Agent, or Firm*—Holland & Hart LLP

[57] ABSTRACT

A humidifier for producing humidified air, particularly for use with a continuous positive air pressure device. The humidifier has an air inlet and outlet. An elongate passageway extending between the air inlet and the air outlet. The passageway is adapted to be partially filled with water so that air passing along the passageway becomes humidified as it passes over the water from the air inlet to the air outlet.

4 Claims, 2 Drawing Sheets

HUMIDIFIER

This is a continuation of application Ser. No. 08/633,413, filed Jun. 10, 1996, now abandoned.

BACKGROUND

The invention relates to a humidifier for producing humidified air, and particularly, although not exclusively, to a humidifier for use with a Continuous Positive Airway Pressure (CPAP) device.

A CPAP device is used in the treatment of obstructive sleep apnea syndrome, which is a disorder characterised by cycles of snoring, obstruction of the upper airway, and partial awakening during the night. In order to treat obstructive sleep apnea, a CPAP device can be used to deliver air under continuous positive pressure to the nasal passages of the patient during sleep. The positive air pressure prevents obstruction of the upper airway so that the patient is not troubled by frequent awakenings during sleep.

In order to prevent drying of the patient's airway during use of a CPAP device, it is known to pass the air through a humidifier before supplying the air to the patient. Humidification can be achieved by simply passing the air over an area of water within a humidifier so that the air absorbs moisture from the water before being delivered to the patient.

When a humidifier is used with a CPAP device, it is convenient to be able to place the CPAP device on top of the humidifier. In this case, it is desirable that the humidifier is designed so as to form a low, generally flat base for supporting the CPAP device. Such a humidifier is known as a low-profile humidifier. Because a low-profile humidifier is of low height, it is more likely to suffer from the problem of entrainment of water droplets in the output air flow to the patient. This problem arises because as the air passes through the humidifier it induces waves on the surface of the water, and water droplets are stripped from the waves by the air flow, and carried by the air flow to the outlet of the humidifier. It is also important when designing a low-profile humidifier to ensure that maximum use is made of the available water surface area. For example, there is no point in providing a large surface area of water within the humidifier if the air flow passes over only a small portion of this area.

The present invention has arisen from attempts to overcome the above difficulties, but is not limited to low-profile humidifiers, or to humidifiers for use with CPAP devices.

SUMMARY OF THE INVENTION

According to the invention there is provided a humidifier for producing humidified air, comprising an air inlet for receiving air to be humidified, an air outlet for discharging humidified air, and an elongate passageway, extending between the air inlet and air outlet, for directing air from the air inlet to the air outlet, the passageway being adapted to be partially filled with water so that air passing along the passageway becomes humidified as it passes over the water from the air inlet to the air outlet.

The use of an elongate passageway between the air inlet and outlet ensures that the airflow passes over substantially the whole of the surface area of the water, so that the whole of the surface area of the water contributes towards humidifying the air flow.

Preferably, the passageway is arranged so as to direct the air from the air inlet to the air outlet along a single path.

This feature ensures that each portion of the surface area of the water contributes equally to the humidifying of the air flow. In an arrangement where the air flow can take a number of different paths between the air inlet and the air outlet, there is a danger that certain paths will contribute more greatly to the humidifying process than others, for example because the air is flowing at different speeds along different paths. Such an arrangement does not make maximum use of the available water surface area.

In a preferred embodiment of the invention, the passageway is divided into a plurality of elongate subpassageways and corner portions, each subpassageway being substantially straight, and the subpassageways being connected end to end along the length of the passageway by the corner portions.

The subpassageways can be integrally formed with the corner portions, so that the passageway as a whole is integrally formed.

This feature avoids the possibility of leaks which might otherwise occur at the connections between the subpassageways and corner portions.

One or more of the corner portions can be generally U-shaped, so that the two subpassageways adjacent the or each generally U-shaped corner portion lie side by side, and substantially parallel with each other.

For example, if the passageway is divided into two, three or four subpassageways, the subpassageways can be arranged to form U-, S- or W-shaped serpentine passageways respectively.

It will be appreciated that the use of generally U-shaped corner portions enables the humidifier to be of compact construction, since the subpassageways lie side by side. This allows a greater number of subpassageways to be accommodated within a humidifier of a given size.

Preferably, the passageway is provided with at least one generally U-shaped corner portion which bulges outwardly at the inside side of the corner defined by the corner portion so as to force air passing through the corner portion outwardly towards the outside side of the corner defined by the corner portion.

This feature ensures that substantially the whole of the surface area of the water in the corner portion is used for humidifying the air flow.

The last corner portion through which air passes before reaching the air outlet will be referred to below simply as "the last corner portion".

Desirably, the last corner portion, whether or not generally U-shaped, increases in width as it passes from the penultimate subpassageway to the last passageway.

It should be understood that the word "width" used above is intended to refer to the dimension of the passageway which lies generally in the plane defined by the surface of the water, and perpendicular to the direction of the air flow along the passageway. Furthermore, the "last" subpassageway is the last passageway through which air in the humidifier passes before reaching the air outlet. The advantage of increasing the width of the passageway at the last corner portion is that it reduces the amount of turbulence in the air flow at the corner portion. It should be noted that most of the air turbulence within the passageway is created at the corner portions, and this turbulence is particularly acute in the case of U-shaped corner portions. The air turbulence creates waves on the water surface which can result in entrainment of water droplets in the air flow at the air outlet, or, if the waves are large enough, indirect spillage of water into the air outlet. By reducing the air turbulence at the last corner portion, the chances of water spillage, or entrainment of water droplets, at the air outlet are greatly reduced.

Preferably, the width of the last corner portion increases gradually as the last corner portion passes from the penultimate subpassageway to the last subpassageway.

Such a gradual increase causes a greater reduction in air turbulence at the corner portion.

In one embodiment of the invention, the ratio of the width of the last corner portion at its inlet side to its width at its outlet side is 9:10.

Preferably, the upper wall, or roof, of the last subpassageway rises gradually along the length of the last subpassageway, towards the air outlet, so as to allow the air outlet to be positioned at a greater height above the water within the last subpassageway.

The gradual increase in height of the roof of the last subpassageway results in a smooth air flow and less air turbulence.

Ideally, the roof of the last subpassageway rises gradually along substantially the whole length of the last subpassageway,.

Similarly, the roof of the first subpassageway may rise gradually along the length of the first subpassageway, towards the air inlet, in the same manner as the roof of the last subpassageway.

In a preferred embodiment of the invention, the passageway terminates at an end wall adjacent the air outlet, and the air outlet is arranged so that it communicates with the interior of the passageway at a location which is spaced away from said end wall.

When the air flow within the passageway creates waves on the surface of the water, it has been found that the water has a tendency to splash against the end wall of the passageway, resulting in a danger of water spilling into the air outlet. It has been found that by spacing the air outlet aperture away from the end wall, the danger of water spilling into the air outlet is greatly reduced.

In a second aspect of the invention there is provided a humidifier for producing humidified air, comprising a chamber adapted to be partially filled with water, the chamber being provided with an air inlet for receiving air to be humidified, and an air outlet for discharging humidified air from the chamber after the air has passed over said water, wherein the air outlet is arranged so that it communicates with the interior of the chamber at a location which is spaced away from all of the chamber walls.

BRIEF DESCRIPTION OF THE DRAWINGS

A preferred embodiment of the invention will now be described, by a way of example only, with reference to the accompanying drawings, in which.

DETAILED DESCRIPTION OF THE INVENTION

Figure 1:
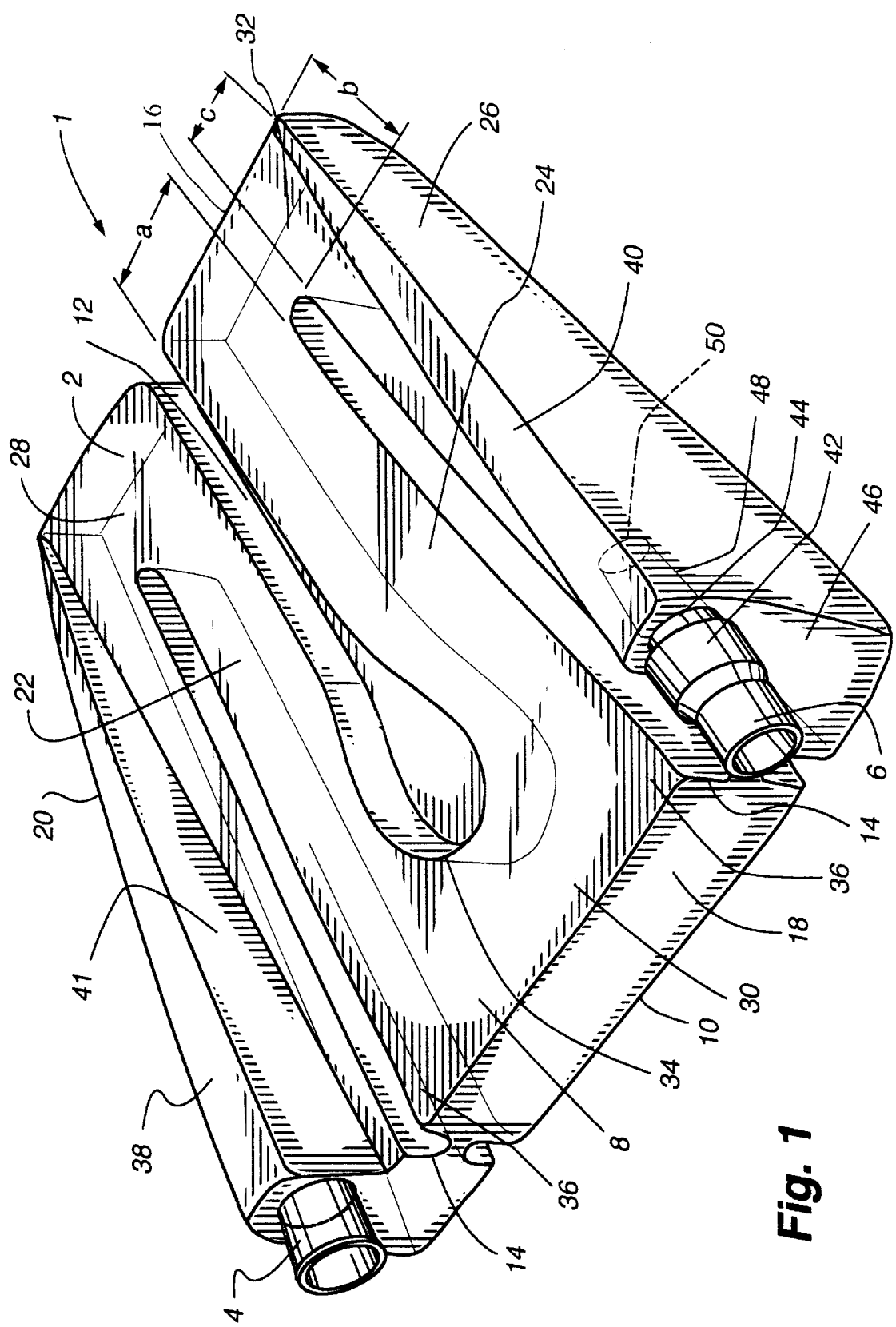
FIG. 1 is a perspective view of a W-shaped humidifier formed from a transparent material.

Referring to FIG. 1, the humidifier 1 comprises a W-shaped elongate passageway 2, an air inlet 4 and an air outlet 6. The humidifier is integrally formed by an extrusion blow-moulding process from translucent, polycarbonate material. During use, the humidifier is partially filled with water, and a use of the translucent material enables the operator to see the water level within the passageway 2 at all times. Furthermore, the integral construction of the humidifier avoids the possibility of leaks of air and water from within the humidifier.

The humidifier is a low-profile humidifier, and is of generally flat, rectangular, box-like construction. The upper and lower walls 8 and 10 of the humidifier are pinched together along a central strip 12 and two outer strips 14 so as to define the shape of the passageway 2. The central strip 12 extends to the rear wall 16 of the humidifier, and the outer strips 14 extend to the front wall 18 of the humidifier, so as to define a generally W-shaped passageway 2 which comprises four subpassageways 20, 22, 24, and 26. The central strip 12 and the two outer strips 14 also provide the humidifier with increased structural rigidity.

The four subpassageways 20, 22, 24, and 26 are each of generally straight, elongate construction. The first subpassageway 20 is connected to the second subpassageway 22 by a first corner portion 28; the second subpassageway 22 is connected to the third (or penultimate) subpassageway 24 by a central corner portion 30; and the third subpassageway 24 is connected to the fourth (or last) subpassageway 26 by a last corner portion 32. All of the corner portions are generally U-shaped, so that the four subpassageways 20, 22, 24, and 26 lie side by side and generally parallel with each other.

The central strip 12 bulges gradually as the central strip 12 passes towards the front wall 18 of the humidifier, to form an enlarged end portion 34 which defines the shape of the inside side of the central corner portion 30. The shape of the enlarged portion 34 ensures that air passing through the central corner portion 30 is forced outwardly towards the corner regions 36 of the central corner portion 30, so that maximum use is made of the available water surface area within the central corner portion 30.

The width of the last corner portion 32 increases gradually from the third subpassageway 24 to the fourth subpassageway 26. For example, the dimensions labelled a, b and c in the drawing can be 40 mm , 45 mm, and 50 mm respectively. The increase in width of the last corner portion 32 reduces air turbulence within the last corner portion 32, and hence reduces the entrainment of water droplets in the air flow, and reduces spillage of water into the air outlet 6.

The roofs 38 and 40 of the first and fourth subpassageways 20 and 26 respectively, rise gradually from the first and last corner portions 28 and 32 to the air inlet 4 and the air outlet 6 respectively. This allows the air inlet 4 and the air outlet 6 to be raised in position with respect to the second and third subpassageways 22 and 24, so that spillage of water into the air inlet 4 or air outlet 6 is less likely to occur. A further advantage of raising the roofs 38 and 40 with respect of the second and third subpassageways 22 and 24 is that a natural hollow or recess 41 is formed between the first and fourth subpassageways 20 and 26. The recess 41 is shaped so as to be of complementary shape to the underside of a CPAP device so that the CPAP device (not shown) fits snuggly on top of the humidifier. It should also be noted that the humidifier is of symmetrical construction, so as to reduce the risk of malfunction, or injury to a patient, if the user should accidentally mistake the air inlet for the air outlet and vice versa.

Figure 2:
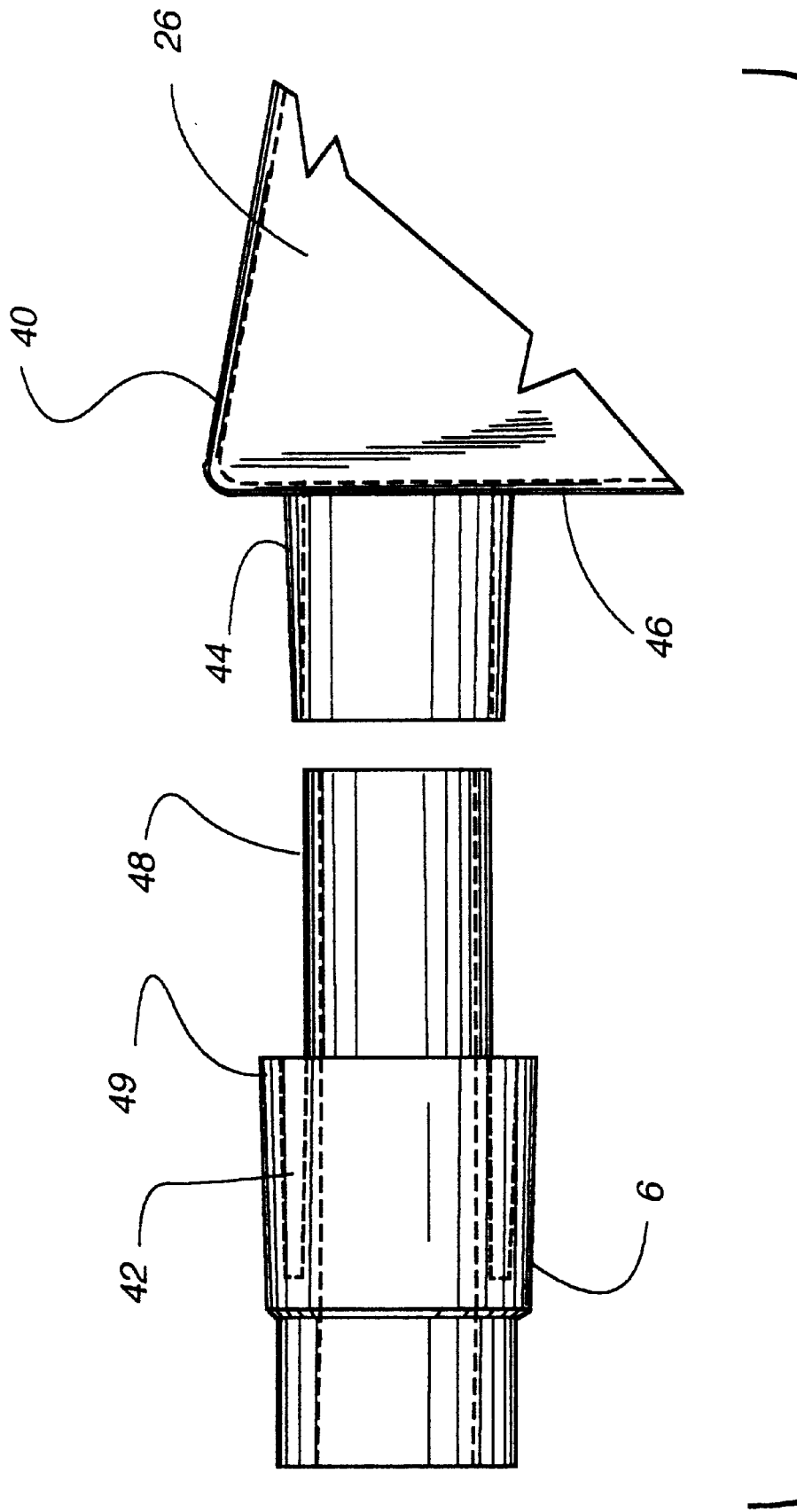
FIG. 2 is a side view showing the outlet attachment of the humidifier in greater detail.

As shown in FIG. 2, the air outlet 6 is formed as an outlet attachment 42 which is attached to a circular tube 44 which projects outwardly from the end wall 46 of the fourth subpassageway 26. The outlet attachment 42 is provided with a tube 48 which projects through the circular tube 44 and into the fourth subpassageway 26, the tube 44 being gripped between the outer surface of the tube 48 and the inner surface of an outer skirt portion 49. The tube 48 extends along a portion of the length of the fourth subpassageway 26. This ensures that air can only leave the fourth subpassageway 26 via the circular aperture 50 at the end of the tube 48, which aperture 50 is spaced away from the end wall 46.

When water waves are formed within the fourth subpassageway 26, the waves have a particular tendency to splash against the end wall 46, resulting in the danger of water spilling into the air outlet 6. It has been found that spacing the aperture 50 of the air outlet 6 away from the end wall 46 overcomes this problem since the water is less turbulent away from the end wall 46. The aperture 50 should preferably be spaced at least 2 cm away from the end wall 46.

It should be appreciated that the idea of spacing the outlet aperture, in this case the aperture 50 of the tube 48, away from the walls of the humidifier is of general applicability, and may be used in other humidifiers, regardless of whether the humidifiers are formed with elongate passageways.

We claim:

1. A humidifier for producing humidified air, comprising a housing having an air inlet for receiving air to be humidified, an air outlet for discharging humidified air, and an elongate passageway extending between the air inlet and air outlet for directing air from the air inlet to the air outlet, the passageway being adapted to be partially filled with water so that air passing along the passageway becomes humidified as it passes over the water from the air inlet to the air outlet, said passageway being divided into a plurality of elongate subpassageways and at least one corner portion, each subpassageway being substantially straight, and the subpassageways being connected end to end along the length of the passageway by one or more of the corner portions and wherein said housing has a relatively low profile, being of generally flat, box-shaped construction, and includes a recess in its upper surface shaped to be of a complementary shape to an underside of a continuous positive airway pressure device adapted to be mounted thereon, wherein the passageway is provided with at least one generally U-shaped corner portion which bulges outwardly at the inside side of the corner defined by the corner portion so as to force air passing through the corner portion outwardly towards the outside side of the corner defined by the corner portion.

2. A humidifier for producing humidified air, comprising a housing having an air inlet for receiving air to be humidified, an air outlet for discharging humidified air, and an elongate passageway extending between the air inlet and air outlet for directing air from the air inlet to the air outlet, the passageway being adapted to be partially filled with water so that air passing along the passageway becomes humidified as it passes over the water from the air inlet to the air outlet, said passageway being divided into a plurality of elongate subpassageways and at least one corner portion, each subpassageway being substantially straight, and the subpassageways being connected end to end along the length of the passageway by one or more of the corner portions and wherein said housing has a relatively low profile, being of generally flat, box-shaped construction, and includes a recess in its upper surface shaped to be of a complementary shape to an underside of a continuous positive airway pressure device adapted to be mounted thereon, including a last passageway being the last passageway through which air in the humidifier passes before reaching the air outlet, wherein the corner portion through which air passes before reaching the air outlet is the last corner portion and said last corner portion increases in width as it passes from the penultimate subpassageway to the last passageway, wherein the upper wall, or roof, of the last subpassageway rises gradually along the length of the last subpassageway, towards the air outlet, so as to allow the air outlet to be positioned at a greater height above the water within the last subpassageway.

3. A humidifier for producing humidified air comprising a housing having an air inlet for receiving air to be humidified, an air outlet for discharging humidified air, and an elongate passageway extending between the air inlet and air outlet for directing air from the air inlet to the air outlet, the passageway being adapted to be partially filled with water so that air passing along the passageway becomes humidified as it passes over the water from the air inlet to the air outlet, said passageway being divided into a plurality of elongate subpassageways and at least one corner portion, each subpassageway being substantially straight, and the subpassageways being connected end to end along the length of the passageway by one or more of the corner portions and wherein said housing has a relatively low profile, being of generally flat, box-shaped construction, and includes a recess in its upper surface shaped to be of a complementary shape to an underside of a continuous positive airway pressure device adapted to be mounted thereon, including a last subpassageway being the last passageway through which air in the humidifier passes before reaching the air outlet, the last subpassageway including a roof or wall rising gradually along substantially the whole length of the last subpassageway towards the air outlet.

4. A humidifier for producing humidified air, comprising a housing having an air inlet for receiving air to be humidified, an air outlet for discharging humidified air, and an elongate passageway extending between the air inlet and air outlet for directing air from the air inlet to the air outlet, the passageway being adapted to be partially filled with water so that air passing along the passageway becomes humidified as it passes over the water from the air inlet to the air outlet, said passageway being divided into a plurality of elongate subpassageways and at least one corner portion, each subpassageway being substantially straight, and the subpassageways being connected end to end along the length of the passageway by one or more of the corner portions and wherein said housing has a relatively low profile, being of generally flat, box-shaped construction, and includes a recess in its upper surface shaped to be of a complementary shape to an underside of a continuous positive airway pressure device adapted to be mounted thereon, including a first passageway being the first subpassageway through which the air in the humidifier passes after leaving the inlet, the first subpassageway including a roof or wall rising gradually along the length of the first subpassageway towards the air inlet.

* * * * *